United States Patent [19]
Cooper et al.

[11] Patent Number: 6,006,131
[45] Date of Patent: *Dec. 21, 1999

[54] DUAL CURRENT PATHWAY ATRIAL DEFIBRILLATION APPARATUS

[75] Inventors: Randolph A. Cooper; Raymond E. Ideker, both of Birmingham; Gregory P. Walcott, Wilsonville, all of Ala.

[73] Assignee: UAB Research Foundation, Birmingham, Ala.

[*] Notice: This patent issued on a continued prosecution application filed under 37 CFR 1.53(d), and is subject to the twenty year patent term provisions of 35 U.S.C. 154(a)(2).

[21] Appl. No.: 08/700,694

[22] Filed: Aug. 13, 1996

[51] Int. Cl.$^6$ .................................................. A61N 1/39
[52] U.S. Cl. .................................................. 607/5
[58] Field of Search ............................. 607/5, 15

[56] References Cited

U.S. PATENT DOCUMENTS

| | | |
|---|---|---|
| 3,825,015 | 7/1974 | Berkovits . |
| 3,995,623 | 12/1976 | Blake et al. . |
| 4,355,646 | 10/1982 | Kallok et al. . |
| 4,365,639 | 12/1982 | Goldreyer . |
| 4,444,195 | 4/1984 | Gold . |
| 4,499,907 | 2/1985 | Kallok et al. . |
| 4,567,901 | 2/1986 | Harris . |
| 4,643,201 | 2/1987 | Stokes . |
| 5,165,403 | 11/1992 | Mehra . |
| 5,209,229 | 5/1993 | Gilli . |
| 5,224,476 | 7/1993 | Ideker et al. . |
| 5,235,977 | 8/1993 | Hirschberg et al. ........................ 607/5 |
| 5,235,978 | 8/1993 | Hirschberg et al. ........................ 607/5 |
| 5,251,624 | 10/1993 | Bocek et al. ............................... 607/6 |
| 5,267,559 | 12/1993 | Jin et al. . |
| 5,269,298 | 12/1993 | Adams et al. . |
| 5,292,338 | 3/1994 | Bardy ........................................ 607/5 |
| 5,304,139 | 4/1994 | Adams et al. ............................ 607/122 |
| 5,304,218 | 4/1994 | Alferness ................................. 607/122 |

(List continued on next page.)

FOREIGN PATENT DOCUMENTS 0 601 340 A1 11/1993 European Pat. Off. ......... A61N 1/05
0653223A2 10/1994 European Pat. Off. .

OTHER PUBLICATIONS

Cooper et al., Internal Cardioversion of Atrail Fibrillation in Sheep, *Atrial Fibrillation: Mechanisms and Therapeutic Straties*, pp. 325–332 (1994).

Luderitz et al., Nonpharmacologic Strategies for Treating Atrial Fibrillation, *The American Journal of Cardiology*, vol. 77, Jan. 25, 1996, pp. 45A–52A.

Cooper et al. Internal Cardioversion of Atrial Fibrillation in Sheep, *Circulation*, vol. 87, No. 5, May 1993, pp. 1673–1685.

Cardiac Rhythm Management Laboratory: In Vivo Study Protocol, Internal Atrial Defibrillation in Sheep Using Sequential Biphasic Waveforms, CRM Laboratory, University of Alabama –Birmingham Medical Center, Oct. 1995.

Feeser et al., Strength–Duration and Probability of Success Curves for Defibrillation with Biphasic Waveforms, *Circulation*, vol. 82, No. 6, Dec. 1990, pp. 2128–2141.

Kroll, Mark W., A Minimal Model of the Monophasic Defibrillation Pulse, *PACE*, vol. 16, Apr. 1993, Part I, pp. 769–777.

*Primary Examiner*—Scott M. Getzow
*Attorney, Agent, or Firm*—Myers Bigel Sibley & Sajovec

[57] ABSTRACT

An implantable system for the defibrillation of the atria of a patient's heart includes a first pair of atrial defibrillation electrodes configured for delivering a first atrial defibrillation pulse along a first current pathway in the heart, and a pulse generator operatively associated with the first pair of atrial defibrillation electrodes for delivering the first atrial defibrillation pulse. A second pair of atrial defibrillation electrodes configured for delivering a second atrial defibrillation pulse along a second current pathway in the heart is also included, with the second current pathway being different from the first current pathway. A pulse generator is operatively associated with the second pair of atrial defibrillation electrodes for delivering the second atrial defibrillation pulse after the first defibrillation pulse.

25 Claims, 8 Drawing Sheets

U.S. PATENT DOCUMENTS

| | | | |
|---|---|---|---|
| 5,312,444 | 5/1994 | Bocek et al. | 607/5 |
| 5,314,430 | 5/1994 | Bardy | 607/5 |
| 5,324,309 | 6/1994 | Kallok | 607/5 |
| 5,332,400 | 7/1994 | Alferness | 607/5 |
| 5,348,021 | 9/1994 | Adams et al. | |
| 5,350,402 | 9/1994 | Infinger et al. | 607/5 |
| 5,387,233 | 2/1995 | Alferness et al. | 607/126 |
| 5,395,373 | 3/1995 | Ayers | 607/8 |
| 5,403,351 | 4/1995 | Saksena | 607/4 |
| 5,403,354 | 4/1995 | Adams et al. | 607/5 |
| 5,405,375 | 4/1995 | Ayers et al. | 607/122 |
| 5,411,527 | 5/1995 | Alt | 607/5 |
| 5,431,681 | 7/1995 | Helland | 607/4 |
| 5,431,683 | 7/1995 | Bowald et al. | 607/5 |
| 5,433,729 | 7/1995 | Adams et al. | 607/5 |
| 5,441,519 | 8/1995 | Sears | 607/5 |
| 5,443,491 | 8/1995 | Snichelotto | 607/122 |
| 5,456,706 | 10/1995 | Pless et al. | 607/122 |
| 5,464,432 | 11/1995 | Infinger et al. | 607/5 |
| 5,470,348 | 11/1995 | Neubauer et al. | 607/68 |
| 5,476,498 | 12/1995 | Ayers | 607/122 |
| 5,476,499 | 12/1995 | Hirschberg | 607/123 |
| 5,486,199 | 1/1996 | Kim et al. | 607/5 |

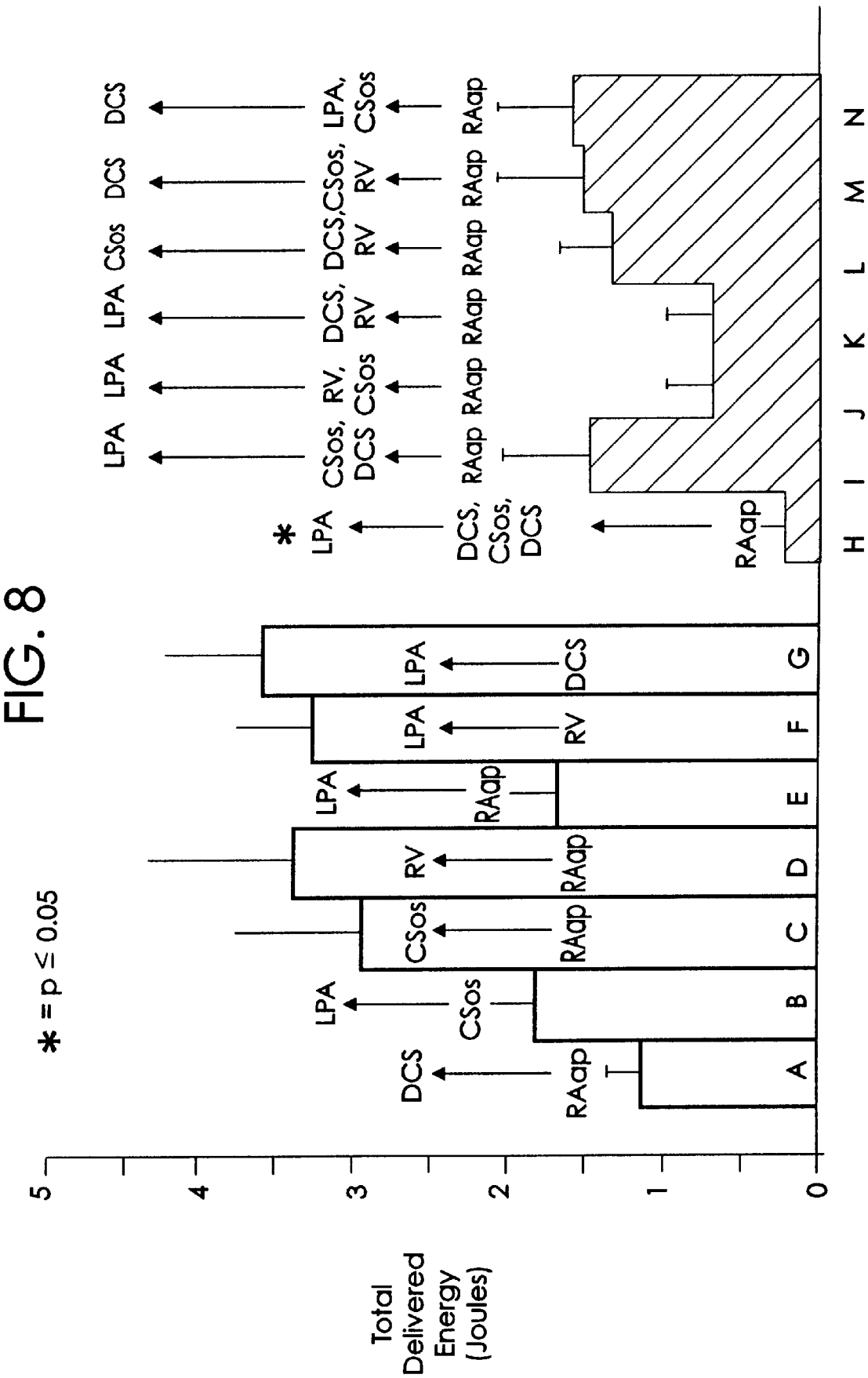

DUAL CURRENT PATHWAY ATRIAL DEFIBRILLATION APPARATUS

FIELD OF THE INVENTION

The present invention relates to an atrial defibrillation method and apparatus in which at least two atrial defibrillation pulses are sequentially delivered along two or more different current pathways.

BACKGROUND OF THE INVENTION

Atrial fibrillation is one of the most common cardiac arrhythmia. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility.

Unlike patients afflicted with ventricular fibrillation, patients afflicted with atrial fibrillation are conscious. The pain associated with the administration of the defibrillation shock can be severe, and there is a need for means of carrying out atrial defibrillation in a manner that is less painful to the patient being treated.

U.S. Pat. No. 5,165,403 to R. Mehra discloses an implantable lead system useful for defibrillating (or "cardioverting") the atria of a patient's heart. In the disclosed system, one electrode is positioned in either the great cardiac vein or coronary sinus of the heart, and another electrode is positioned in either the right atrium or superior vena cava of the heart. Configurations for reducing the pain associated with defibrillation are not disclosed.

U.S. Pat. No. 5,209,229 to Gilli discloses an implantable atrial defibrillation device employing multiple implantable electrodes. Upon detection of atrial fibrillation, a first electrode configuration is selected and a defibrillation shock administered. If atrial fibrillation remains after that shock, then a second electrode configuration is selected and a second defibrillation shock administered. Multiple defibrillation pulse administrations are only used when the initial defibrillation pulse fails, and not as a means to reduce pain associated with atrial defibrillation.

In view of the foregoing, an object of the present invention is to provide methods and apparatus for carrying out atrial defibrillation that will reduce the pain associated therewith.

A further object of the present invention is to provide methods and apparatus for carrying out atrial defibrillation that will reliably treat atrial fibrillation.

A still further object of the present invention is to provide methods and apparatus for treating atrial fibrillation that minimizes the extent of the surgical intervention involved in implanting the necessary defibrillation electrodes, and minimizes the complexity involved in implanting the necessary defibrillation electrodes.

SUMMARY OF THE INVENTION

An implantable system for the defibrillation of the atria of a patient's heart is described herein. The system includes a first pair of atrial defibrillation electrodes configured for delivering a first atrial defibrillation pulse along a first current pathway in the heart, and a pulse generator operatively associated with the first pair of atrial defibrillation electrodes for delivering the first atrial defibrillation pulse. A second pair of atrial defibrillation electrodes configured for delivering a second atrial defibrillation pulse along a second current pathway in the heart is also included, with the second current pathway being different from the first current pathway. A pulse generator is operatively associated with the second pair of atrial defibrillation electrodes for delivering the second atrial defibrillation pulse after the first defibrillation pulse.

The second defibrillation pulse is delivered without intervening monitoring of the efficacy of the first defibrillation pulse. The present invention thus provides a method of atrial defibrillation by sequentially delivering two atrial defibrillation pulses along different current pathways to the atria of a patient afflicted with atrial fibrillation. The energy of the pulses and the pain associated therewith is thereby reduced.

As will be apparent to those skilled in the art, the first and second pulses described above may be followed by additional pulses if desired. Additional pulses may be along different current pathways, or along the first or second current pathways. The apparatus described herein may be extended to provide for the administration additional pulses in accordance with known techniques.

Multiple defibrillation pulses have been used in the treatment of ventricular fibrillation (see, e.g., U.S. Pat. No. 5,224,476 to Ideker and Guse and references cited therein) where pain reduction is not a compelling object. Multiple defibrillation pulses along different current pathways have not heretofore been suggested in the treatment of atrial fibrillation.

BRIEF DESCRIPTION OF THE DRAWINGS

FIG. 8 is a bar graph illustrating the total delivered energy in Joules (given on the vertical axis) required to achieve atrial defibrillation by various single current pathways (bars "A" through "G") and dual current pathways (bars "H" through "N") in adult sheep. Current pathways are indicated above each bar, with dual current pathways being separated by a comma. "RAap" means right atrial appendage, "DCS" means distal coronary sinus, "CSos" means proximal coronary sinus, "LPA" means left pulmonary artery, and "RV" means right ventricular apex.

DETAILED DESCRIPTION OF THE PREFERRED EMBODIMENTS

Figure 1:
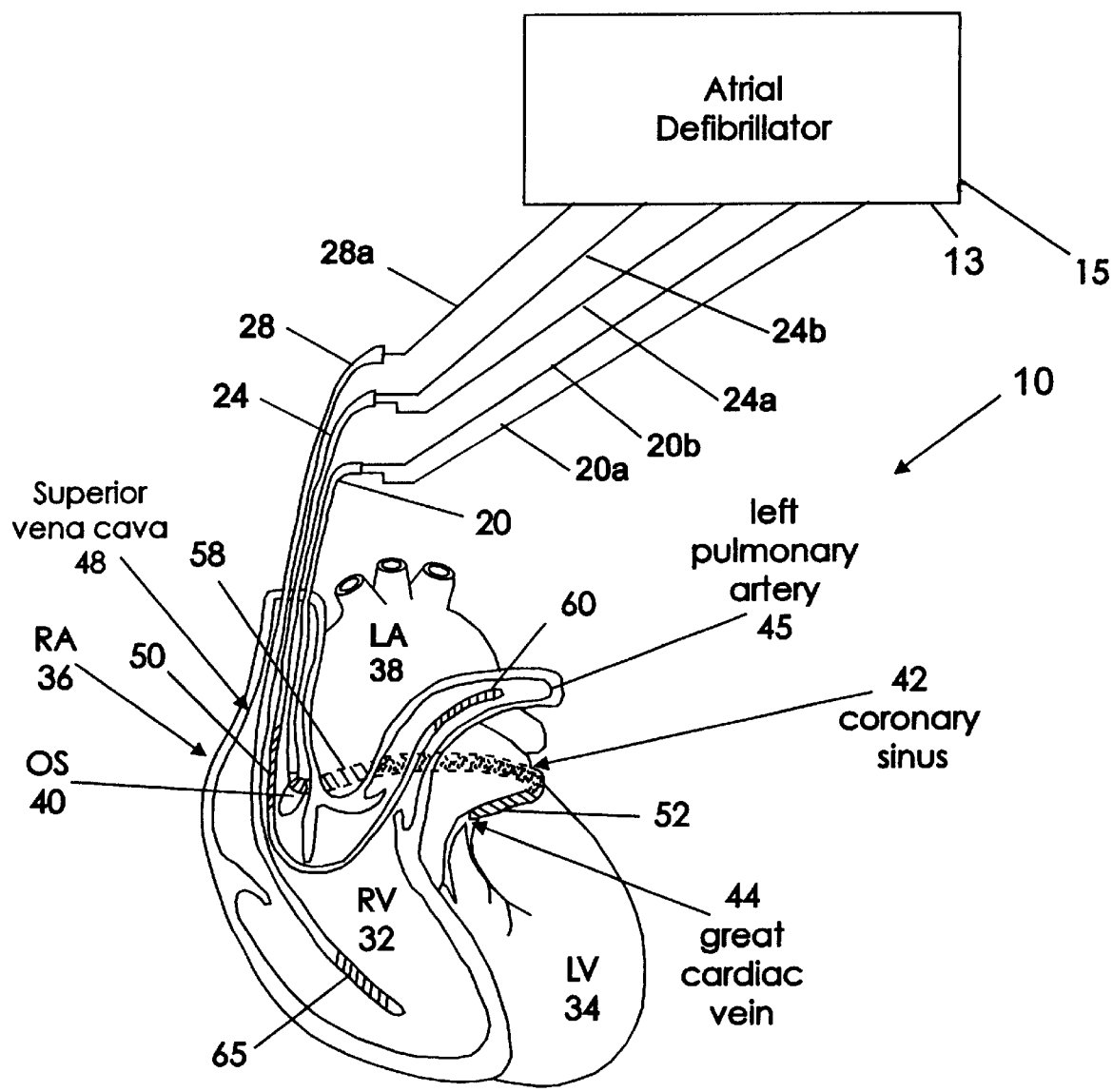
FIG. 1 illustrates a first embodiment of an implantable defibrillation system of the present invention, where a first catheter carries defibrillation electrodes positioned in the proximal coronary sinus and in the distal coronary sinus, a second catheter carries defibrillation electrodes positioned in the right atrium and in the pulmonary artery, and a third catheter carries a monitoring electrode positioned in the right ventricle.

Anatomically, the heart includes a fibrous skeleton, valves, the trunks of the aorta, the pulmonary artery, and the muscle masses of the cardiac chambers (i.e., right and left atria and right and left ventricles). The schematically illustrated portions of the heart 30 illustrated in FIGS. 1–5 include the right ventricle "RV" 32, the left ventricle "LV" 34, the right atrium "RA" 36, the left atrium "LA" 38, the superior vena cava 48, the coronary sinus "CS" 42, the great cardiac vein 44, and the coronary sinus ostium or "os" 40.

The driving force for the flow of blood in the heart comes from the active contraction of the cardiac muscle. This contraction can be detected as an electrical signal. The contraction travels in a wave propagation pattern which begins at the cells of the SA node and the surrounding atrial myocardial fibers, and then travels into the atria and subsequently passes through the AV node and, after a slight delay, into the ventricles.

The beginning of a cardiac cycle is initiated by a P wave, which is normally a small positive wave. The P wave induces depolarization of the atria of the heart. The P wave is followed by a cardiac cycle portion which is substantially constant with a time constant on the order of 120 milliseconds ("ms").

The "QRS complex" of the cardiac cycle occurs after the substantially constant portion. The dominating feature of the QRS complex is the R wave which is a rapid positive or negative deflection. The R wave generally has an amplitude greater than any other wave of the cardiac cycle, and has a spiked shape of relatively short duration with a sharp rise, a peak amplitude, and a sharp decline. The R wave is the depolarization of the ventricles and therefore, as used herein, the term "ventricle activations" denotes R waves of the cardiac cycle. The QRS complex is completed by the S wave, which is typically a small deflection that returns the cardiac signal to baseline. Following the S wave, the T wave occurs after a delay of about 250 ms. The T wave is relatively long in duration (e.g., about 150 ms). The cardiac cycle between the S wave and the T wave is commonly referred to as the ST segment. The T wave is a sensitive part of the cardiac cycle, during which an atrial defibrillation shock is to be avoided, in order to reduce the possibility of an induced (and often fatal) ventricular fibrillation. The next cardiac cycle begins with the next P wave. The typical duration of a complete cardiac cycle is on the order of about 800 ms.

In overview, an implantable system for the defibrillation of the atria of a patient's heart comprises (a) a first pair of atrial defibrillation electrodes configured for delivering a first atrial defibrillation pulse along a first current pathway in the heart; (b) a pulse generator operatively associated with the first pair of atrial defibrillation electrodes for delivering the first atrial defibrillation pulse; (c) a second pair of atrial defibrillation electrodes configured for delivering a second atrial defibrillation pulse along a second current pathway in the heart, with the second current pathway different from the first current pathway; and (d) a pulse generator operatively associated with the second pair of atrial defibrillation electrodes for sequentially delivering the second atrial defibrillation pulse after the first defibrillation pulse. The electrode pairs may be placed in a variety of different locations, as long as different current pathways for the first and second pulse are thereby achieved. A single electrode may participate in more than one electrode pair, so that, for example, two current pathways are achieved through three defibrillation electrodes. Additional electrodes may be tied together to one member of an electrode pair to provide a single pole, if so desired, and additional electrodes may be provided for following the first and second shocks with additional shocks.

In one embodiment of the invention, the first pair of atrial defibrillation electrodes comprises a defibrillation electrode positioned in the right atrium or superior vena cava of the heart, and a defibrillation electrode positioned in the distal coronary sinus or great cardiac vein of the heart. The electrodes themselves may be configured for positioning in the indicated location. Numerous alternatives for the second pair of atrial defibrillation electrodes forming a second pathway are possible. For example, the second pair of atrial defibrillation electrodes may comprise:

(A) a defibrillation electrode positioned in the proximal coronary sinus of the heart, and a defibrillation electrode positioned anterior to the left atrium of the heart (e.g., in the left pulmonary artery, or on the external surface of a device implanted subcutaneously in the left thoracic region of the patient):

(B) a defibrillation electrode positioned in the left pulmonary artery of the heart, and a defibrillation electrode positioned in the right ventricle of the heart;

(C) a defibrillation electrode positioned in the distal coronary sinus of the heart, and a defibrillation electrode positioned in the right ventricle of the heart;

(D) a defibrillation electrode positioned in the left pulmonary artery of the heart, and a defibrillation electrode positioned in the right atrium of the heart;

(E) a defibrillation electrode positioned in the left pulmonary artery of the heart, and a defibrillation electrode positioned in the distal coronary sinus of the heart (the electrode positioned in the distal coronary sinus may optionally be tied together with an electrode positioned in the right atrium as one pole);

(F) a defibrillation electrode positioned in the proximal coronary sinus of the heart, and a defibrillation electrode positioned in the right atrium of the heart; or (G) a defibrillation electrode positioned in the proximal coronary sinus of the heart, and a defibrillation electrode positioned in the distal coronary sinus of the heart (the electrode positioned in the distal coronary sinus may optionally be tied together with an electrode positioned in the right atrium as one pole).

Again, the electrodes may be configured for positioning in the indicated locations, and numerous variations on the foregoing will be readily apparent to those skilled in the art. For example, the first defibrillation pulse could be delivered by the second pair of electrodes indicated above, and the second defibrillation pulse could be delivered by the first pair of electrodes indicated above (in which case the indicated second pair of electrodes serves as the "first pair" and the indicated first pair serves as the "second pair"). In addition, multiple electrodes may be implanted to provide three, four, or five or more different alternative electrode pairs and current paths, and the electrode coupling to the pulse generator switched after implantation of the electrodes to optimize the electrode configuration for a particular patient.

FIG. 1 illustrates a first embodiment of an atrial defibrillation system of the instant invention. The atrial defibrillator 10 of FIG. 1 includes an implantable housing 13 which contains a hermetically sealed electronic circuit 15. The atrial defibrillator also includes a first catheter 20, a second catheter 24, and a third catheter 28, all of which are insertable into the heart 30 without the need for surgical incision. The term "catheter" as used herein includes "stylet" and is also used interchangeably with the term "lead". Each of the catheters 20, 24, 28 contain electrode leads 20a, 20b, 24a, 24b, 28a, respectively for connecting at least one electrode to the electronic circuit 15 in the housing.

In the embodiment of FIG. 1, the implantable defibrillation system includes a first defibrillation electrode 50 configured for positioning in the right atrium (RA) 36 or superior vena cava 48. Also illustrated in sectional view is the interior of the right ventricle (RV) 32, along with the exterior of the left atrium (LA) 38 and the exterior of the left ventricle (LV) 34. A second defibrillation electrode 52 is configured for positioning in the distal coronary sinus (DCS) 42 or great cardiac vein 44. A pulse generator which is part of the electronic circuit 15 enclosed in the implantable housing 13 is connected to and couples the first pair of electrodes 51 (50, 52) via leads 20, 24. Thus, a first pair of electrodes 51 thereby provides a first current pathway 53 for delivering a first atrial defibrillation pulse therebetween.

A second pair of electrodes are disposed to provide a second current pathway 55 different from the first current pathway 53. As illustrated in FIG. 1, a second pair consisting of a third electrode 58 and a fourth electrode 60. As illustrated, the third electrode 58 is configured for positioning in the proximal coronary sinus (PCS) 42 and the fourth electrode 60 is configured for positioning in the left pulmonary artery (LPA) 45. A second pulse is generated by the pulse generator and delivered via leads 20, 24 to be delivered by the electrically coupled or paired PCS and LPA electrodes 58, 60.

As illustrated in FIG. 1, the first lead 20 in this embodiment comprises an endocardial transvenous elongate lead having electrodes 52 and 58 arranged for establishing electrical communication with the opposing (or paired) electrode as described hereinabove. The lead is typically enclosed in a catheter and flexibly arranged to be fed through the superior vena cava 48, into the right atrium 50, and then into the coronary sinus os 40 and advanced into the coronary sinus so that the distal electrode 52 in the distal coronary sinus (DCS) is within the CS adjacent the LV 34 and beneath the LA, or within the great cardiac vein 44 adjacent the left ventricle 34. The proximal CS electrode (described in this embodiment as the third electrode, supra) 58 is spaced apart from the DCS electrode such that when the DCS electrode is properly positioned, the PCS electrode remains in the CS.

The second lead 24 in FIG. 1 comprises an endocardial transvenous elongate lead having electrodes 50 and 60 arranged for establishing electrical communication with an opposing or paired electrode to provide an appropriate shock pulse therebetween. As such, the lead is typically enclosed in a catheter and flexibly arranged to be fed into the superior vena cava 48 and advanced into the pulmonary artery 45. The fourth electrode or pulmonary artery electrode is preferably on the tip or tip portion of the lead 24 so as to be insertably positioned in the pulmonary artery adjacent the LA 38. Upon proper placement, the first electrode or RA electrode 50 is spaced on the lead apart from the LPA electrode 60 so that when in place it is positioned in the RA 36 or superior vena cava 48.

Also illustrated in FIG. 1 is a fifth electrode 65 configured for positioning in the apex portion of the RV 32. This electrode is typically a monitoring electrode for providing the selected cardiac wave signals, i.e., P, R, or T via associated lead line 28 to a synchronization monitor 72 and a controller in the electronic circuit 15 which allows the controller 74 to synchronize the delivery of the atrial stimulation pulses in response to the detected cardiac or ventricular signals to minimize the possibility of induced ventricular fibrillation.

Figure 2:
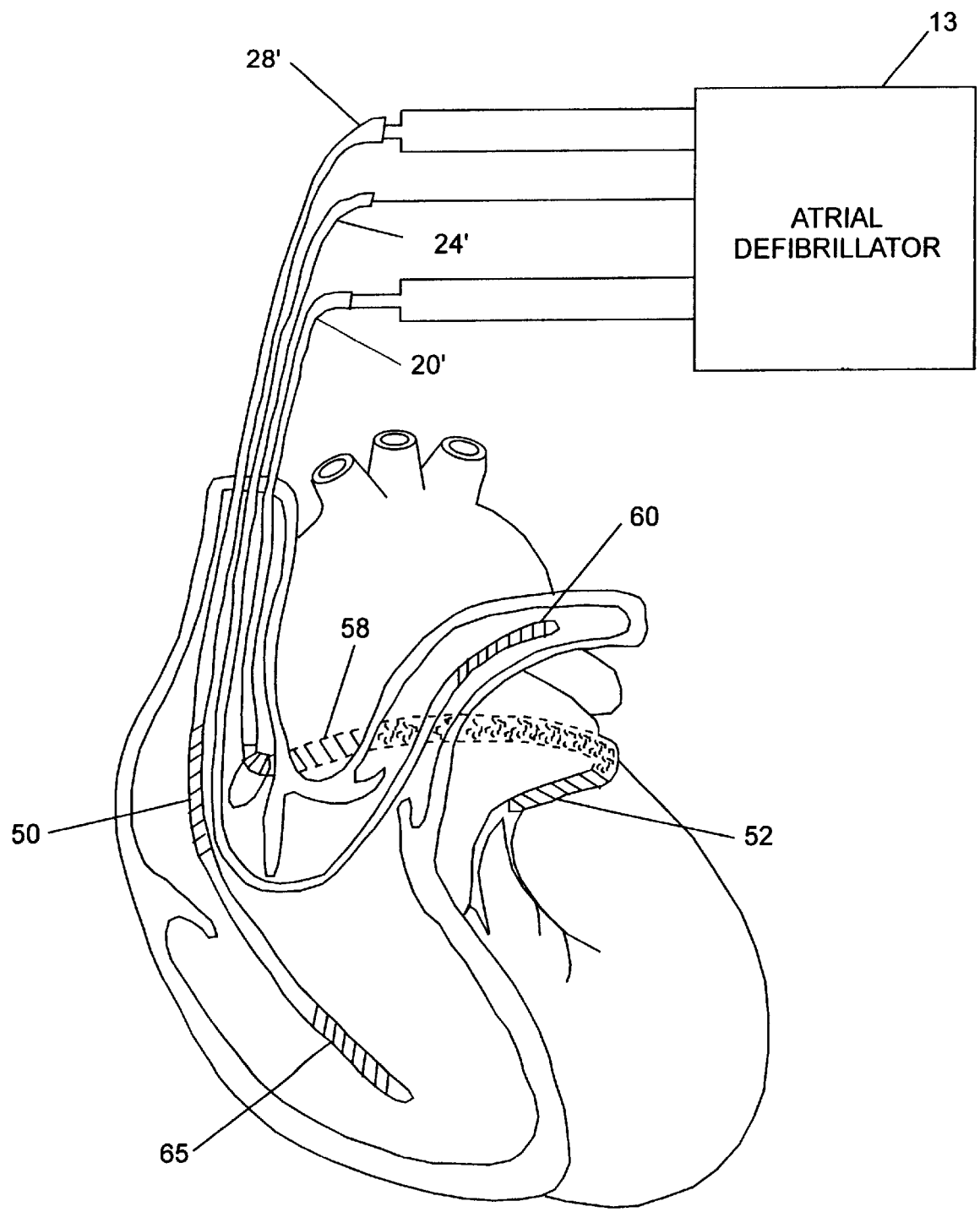
FIG. 2 illustrates a second embodiment of the present invention, where a first catheter carries defibrillation electrodes positioned in the proximal coronary sinus and in the distal coronary sinus, a second catheter carries a defibrillation electrode positioned in the pulmonary artery, and a third catheter carries a monitoring electrode positioned in the right ventricle and a defibrillation electrode positioned in the right atrium.
Figure 3:
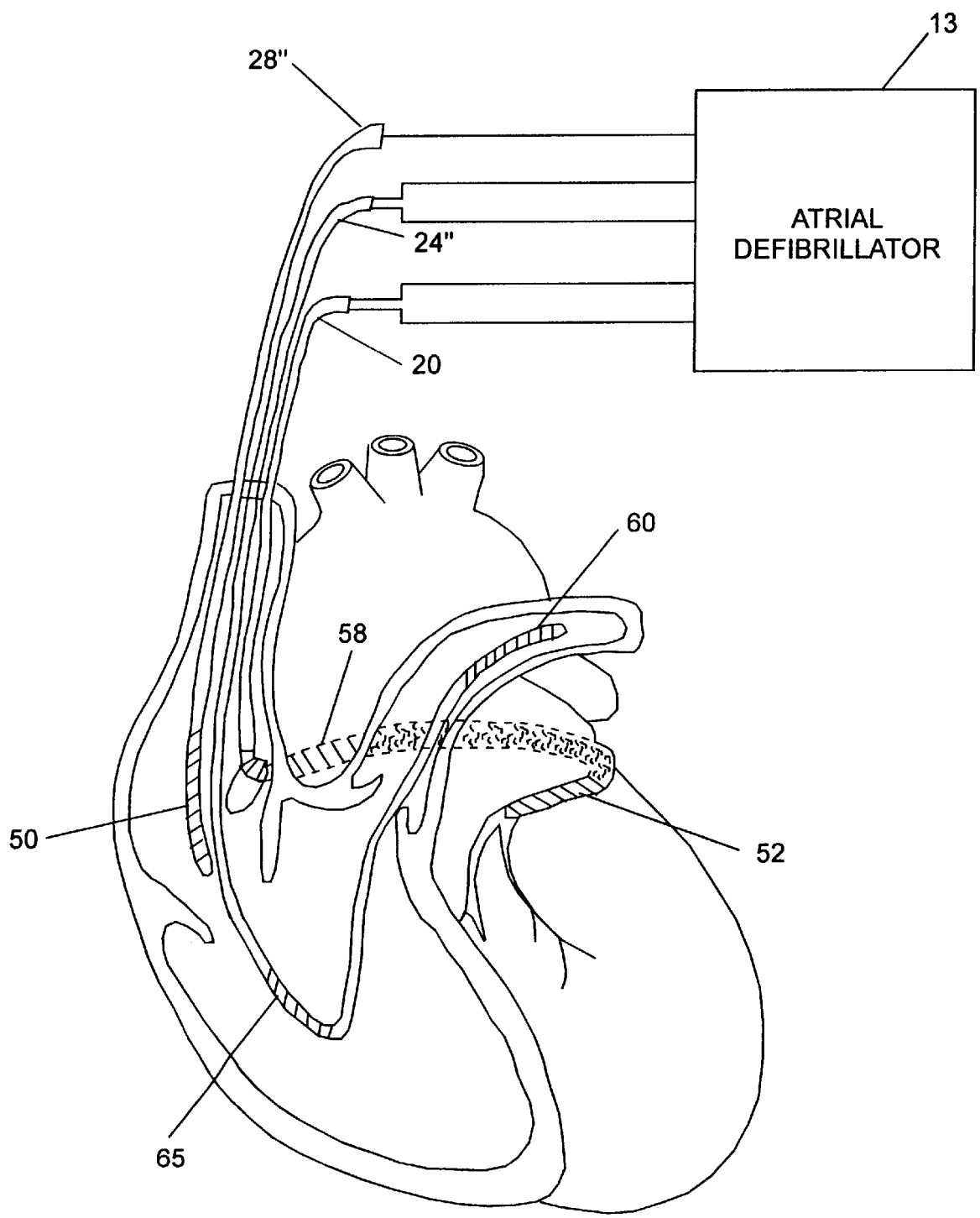
FIG. 3 illustrates a third embodiment of the present invention, where a first catheter carries defibrillation electrodes positioned in the proximal coronary sinus and in the distal coronary sinus, a second catheter carries a defibrillation electrode positioned in the right atrium, and a third catheter carries a monitoring electrode positioned in the right ventricle and a defibrillation electrode positioned in the pulmonary artery.
Figure 4:
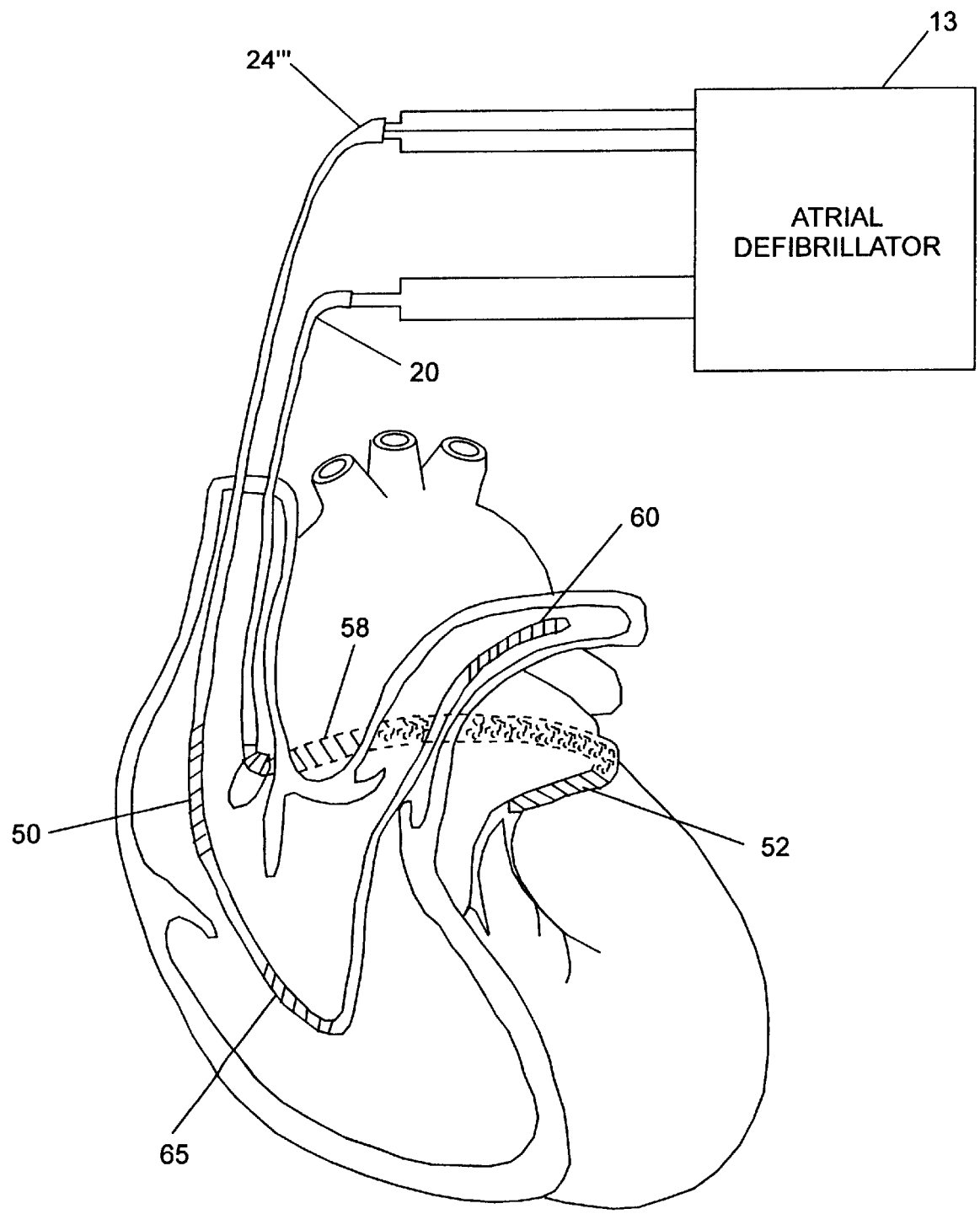
FIG. 4 illustrates a fourth embodiment of the present invention, where a first catheter carries defibrillation electrodes positioned in the proximal coronary sinus and in the distal coronary sinus, and a second catheter carries a defibrillation electrode positioned in the right atrium, a monitoring electrode positioned in the right ventricle, and a defibrillation electrode positioned in the pulmonary artery.

FIGS. 2–4 are similar to FIG. 1 above, and illustrate alternate embodiments of lead and electrode placements, where the electrode pairs and relative placement for delivering the stimulation shock pulses remains the same. Like components bear like numbers to FIG. 1 above. It will be appreciated by those of skill in the art that the particular leads on which the electrodes are arranged does not affect the electrical coupling of the respective opposing electrode. The electrical coupling is provided by a controller and switch in the electronics circuit (discussed below). In each embodiment it is preferable, but not essential, that the PCS and DCS electrodes remain on the same lead for easier insertion, here shown as the first lead or catheter 20.

FIG. 2 illustrates an embodiment of the invention where the second lead or catheter 24' includes the LPA electrode 60 on the distal end, preferably the tip, of the lead. The third lead or catheter 28' includes the RA and RV electrodes 50, 65, positioned proximally and distally respectively.

FIG. 3 illustrates a different embodiment of the second and third leads or catheters 24", 28". The second catheter 24" includes proximally positioned RV and distally positioned LPA electrodes 65, 60; the third catheter 28" includes a RA (or SVC) electrode 50 which is positioned as a distal tip electrode thereof.

FIG. 4 illustrates an embodiment which employs only two catheters or leads 20, 24'''. The second lead 24''' includes three electrodes, a distal LPA electrode 60, an intermediate RV electrode 65 and a proximal RA (or SVC) electrode 50.

Figure 5:
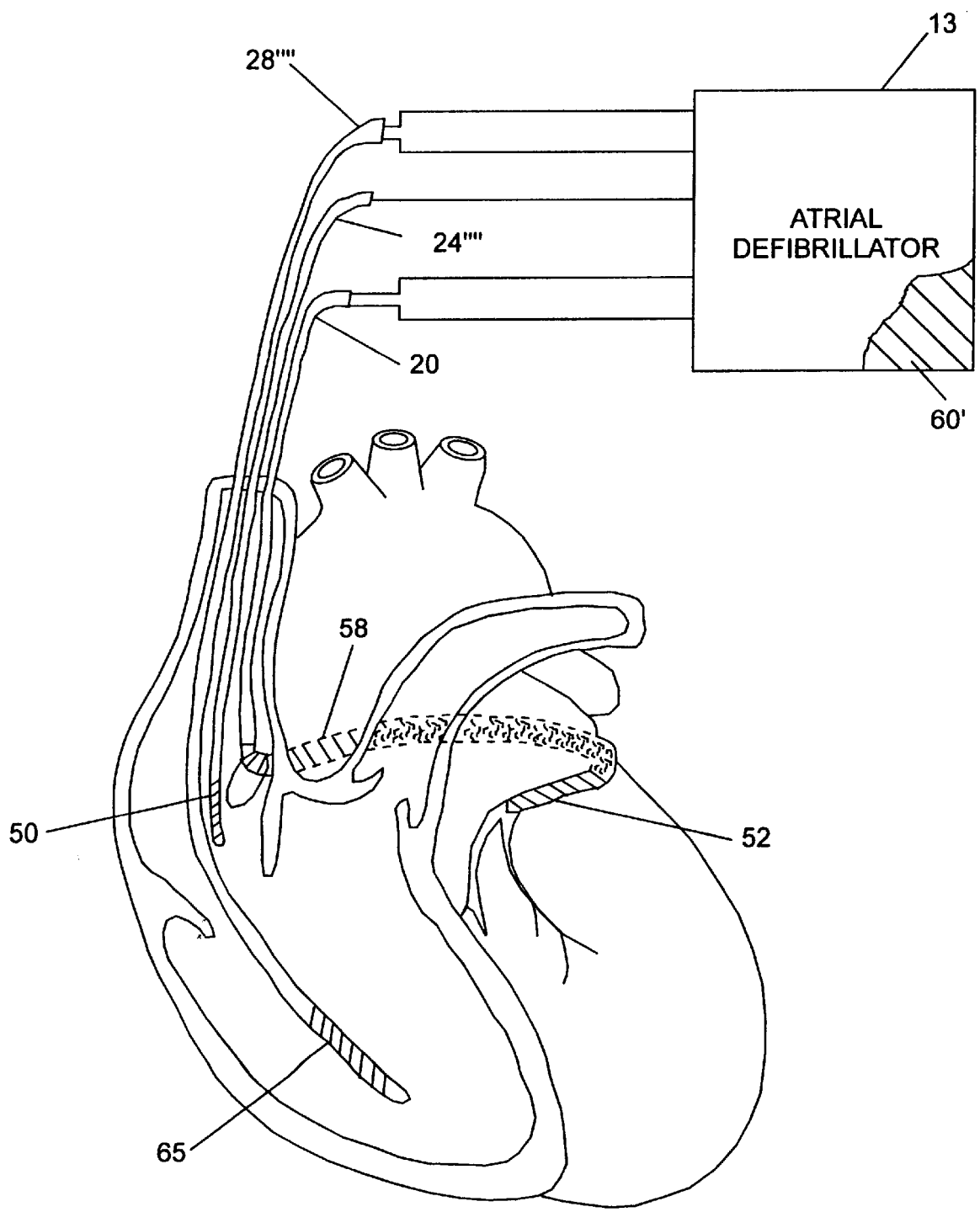
FIG. 5 illustrates a fifth embodiment of the invention similar to the first embodiment illustrated in FIG. 1, except that the defibrillation electrode located on the second catheter and positioned in the pulmonary artery has been eliminated, and a defibrillation electrode has been provided on the surface of the defibrillator.

FIG. 5 is similar to FIG. 1, but illustrates an alternate embodiment of the LPA electrode 60 as well as alternate lead or catheter configurations. The LPA electrode 60 is replaced by (or in the alternative supplemented with) an electrode comprising an active external portion 60' of the housing 13, which is preferably implanted anterior to the left atrium. In this embodiment, the housing electrode 60' is typically paired with the PCS electrode 58 and is configured to provide a stimulation pulse therebetween as directed by the controller and electronic circuit.

Figure 6:
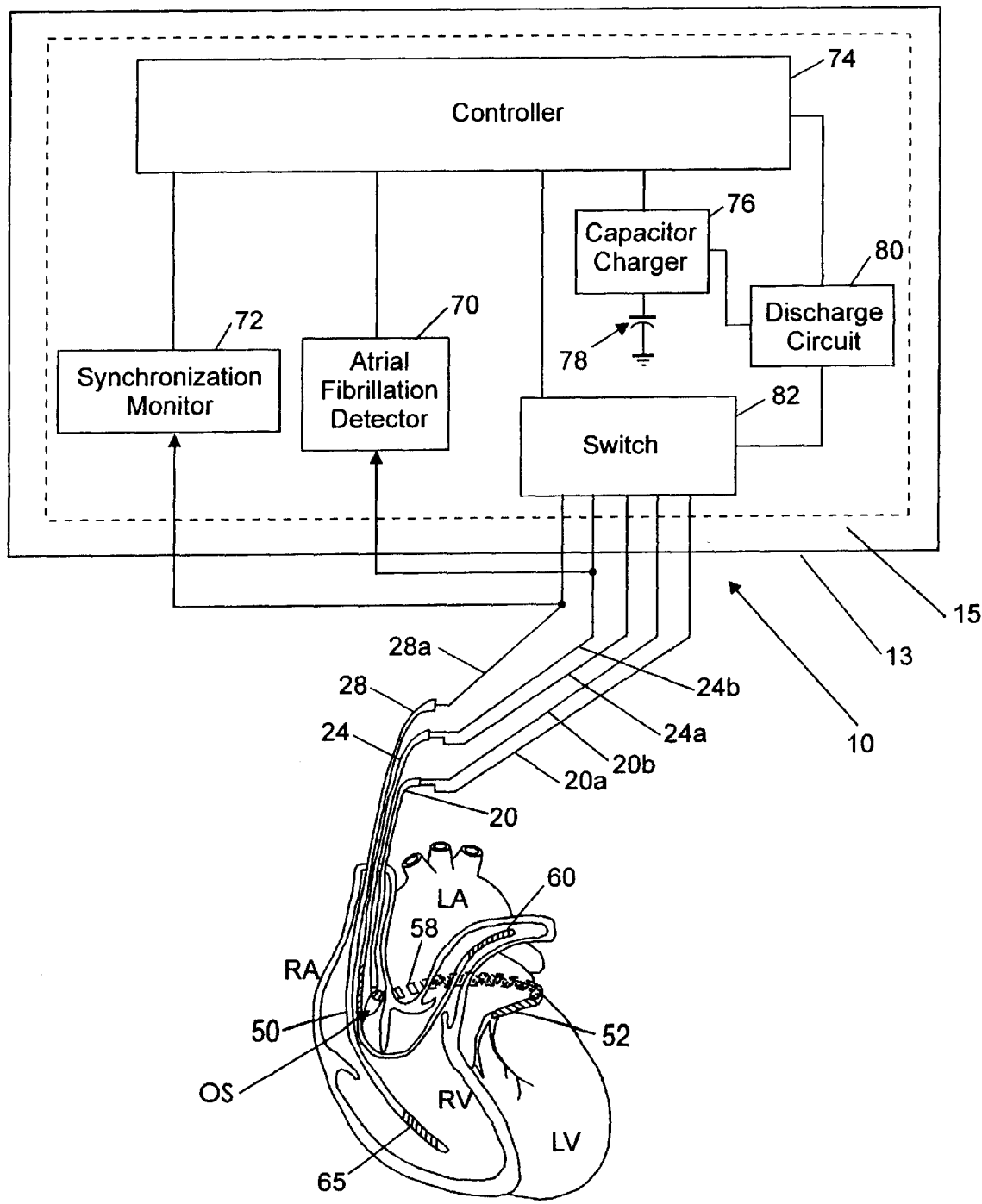
FIG. 6 schematically illustrates the electronic circuitry of an implantable atrial defibrillator of the present invention.

FIG. 6 illustrates one example of an implantable housing 13 containing an electronic circuit 15, which includes one or more amplifiers (not shown) for amplifying sensed cardiac signals. The amplified signals are analyzed by an atrial fibrillation detector 70 which determines if atrial fibrillation is present. The atrial fibrillation detector 70 may be one of several known to those skilled in the art. Although, as illustrated, a sensing signal is provided by the RA electrode 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the atrial fibrillation detector may be a plurality of lines which if providing only sensing will provide an input to the detector.

The defibrillation electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 15 also includes a cardiac cycle monitor ("synchronization monitor 72") for providing synchronization information to the controller 74. As discussed below, the synchronization is typically provided by sensing cardiac activity in the RV, but may also include other sensing electrodes which can be combined with the defibrillation electrodes or employed separately to provide additional assurance that atrial stimulation shock pulses are not delivered during sensitive portions of the cardiac cycle so as to reduce the possibility of inducing ventricular fibrillation.

Upon a signal from the atrial fibrillation detector 70, the controller 74, in turn, signals a capacitor charging circuit 76 which then charges the storage capacitor 78 to a predetermined voltage, typically from a battery source (not shown). The discharge of the capacitor is controlled by the controller 74 and/or a discharge circuit 80. The controller, based on information from the synchronization monitor 72, typically allows or directs the preselected shock pulse to be relayed to either a discharge circuit for further processing (i.e., to further shape the waveform signal, time the pulse, etc.) or directly to a switch. The controller also typically controls the proper selection of the predetermined defibrillation electrode pair(s) to direct the switch to electrically activate a desired electrode pair to align the predetermined electric shock pulse pathway through which the shock pulse is provided. As an alternative to an atrial defibrillation detector, the defibrillation pulses may be triggered by an external signal administered by a physician, with the physician monitoring the patient for the appropriate time of administration.

As noted above, the instant invention provides two separate shock pulses to two separate current pathways determined by the electrode pair arrangement also as discussed above. Therefore, it will be appreciated by those of skill in the art that the capacitor 78 may be a single capacitor or a bank of parallel capacitors sufficiently charged and sized to be able to provide at least two separate shock pulses to predetermined electrodes positioned in the heart. Additionally, the capacitor 78 can be two or more separately charged capacitors (or bank of parallel capacitors) on separate lines to provide two separate and sequential shock pulses as controlled by the controller 74 and/or the discharge circuit 80. However, it is preferred that the capacitor 78 be a relatively large capacitor for insuring sufficient charge and decay period (i.e., long time constant and low tilt) to provide sufficient energy for two shock pulses. For example, a capacitor with capacitance in the range of 200–1000 $\mu f$ or more, having an associated time constant in the range of 30 ms, would typically be charged to approximately 100–200 volts and would deliver a V(peak) in a typical first waveform of about 50–100 volts leading edge. If additional shocks beyond two are administered, then a larger capacitor may be employed. In the alternative wherein the electronic package employs a circuit to further shape the waveform, the capacitor may be charged to a higher voltage range (such as around 200 V).

In one embodiment of the invention, the pulse generator includes a single capacitor 78, and the controller 74 includes a switch (e.g., a crosspoint switch) operatively associated with that capacitor. The switch is configured to provide a biphasic pulse (i.e., a first phase of a pulse of a predetermined polarity followed by a second phase of a pulse of reversed polarity) as the first atrial defibrillation pulse and a biphasic pulse as the second atrial defibrillation pulse.

The controller 74 delivers a preselected electrical pulse to predetermined electrode pairs through a switch 82 which is preferably programmable. The capacitor charger 76, capacitor 78, controller 74, discharge circuit 80 and switch 82 thus form an electrical pulse generator. Therefore, it will be appreciated that in operation, in response to an input from the atrial fibrillation detector 70, the controller 74 controls the pulse generator to synchronize the delivery of the timed pulse output to the proper electrode pair in accordance with the cardiac cycle information received from the synchronization monitor 72 and the specific electrode configuration employed by the device. Further, when employing a biphasic waveform, it will be appreciated by those of skill in the art that the pulse generator also includes a crosspoint switch to switch the polarity of the electrode pair for delivery of the second (inverted or negative) waveform phase. It is also preferable that the electronic package include a receiver/transmitter coupled to the internal controller 74 for communicating with an external controller. Thus the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment of the invention, the switch 82 is programmable (e.g., by remote control such as by a radio signal) to alter the coupling of the pulse generator to the atrial defibrillation electrodes. This feature is advantageously employed when multiple electrodes are implanted so that the electrode pairs that deliver the first and second atrial defibrillation pulses may be changed to optimize the technique for a particular patient.

The energy of the first atrial defibrillation pulse is preferably not greater than 8 joules, more preferably not greater than 6 joules, still more preferably not greater than 4 joules, and most preferably not greater than 2 joules. The energy of the second atrial defibrillation pulse is typically not greater than the energy of the first defibrillation pulse (although such a result is possible where a dual capacitor design is employed), and is preferably not greater than 8 joules, more preferably not greater than 6 joules, still more preferably not greater than 4 joules, and most preferably not greater than 2 joules. The second atrial defibrillation pulse preferably follows the first atrial defibrillation pulse by 0 to 500 milliseconds, and more preferably follows the first atrial defibrillation pulse by 0 to 200 milliseconds. In the alternative, the second atrial defibrillation pulse may overlap the first atrial defibrillation pulse, for example by from one fourth to three fourths of the total shock duration (the duration of both shocks in series). The duration of each shock may be, for example, from three to twenty milliseconds, with total shock duration being, for example, from four and one half to forty milliseconds.

Figure 7A:
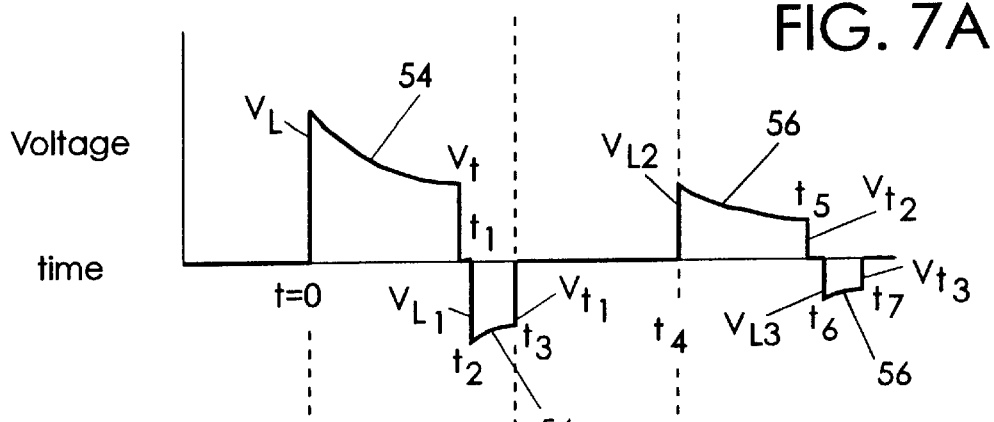
FIG. 7A illustrates a decaying exponential waveform that can be used to carry out the present invention. Voltage is given on the vertical axis and time is given on the horizontal axis, with negative voltages being indicated by waveforms below the horizontal axis.

FIGS. 7A through 7D illustrate exemplary waveforms that can be used to carry out the present invention. Voltage is given on the vertical axis and time is given on the horizontal axis of each figure. The particular waveform of the defibrillation pulse is not critical, and any waveform can be used. The typical voltage waveform delivered by a capacitor is a decaying exponential waveform 54, 56 with the leading edge voltage of the second pulse $V_{L2}$ being less than or equal to the trailing edge voltage Vt1 of the first pulse and such a waveform is illustrated in FIG. 7A. As illustrated, the first pulse waveform 54 is a biphasic asymmetric waveform with a longer first phase and a shorter second phase: for example, a 5–15 millisecond (ms) first phase, and a 2–10 ms second phase. More preferably, the biphasic waveform is about a 3 ms/–1 ms pulse waveform.

Figure 7B:
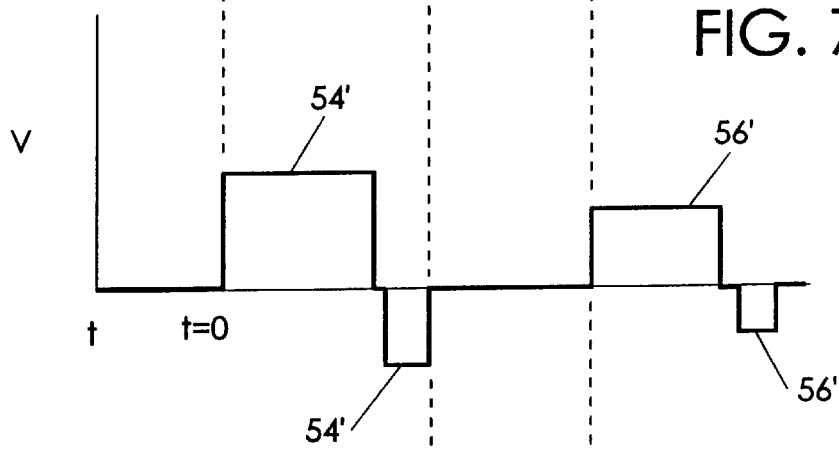
FIG. 7B is similar to FIG. 7A, and illustrates a stepped input waveform.
Figure 7C:
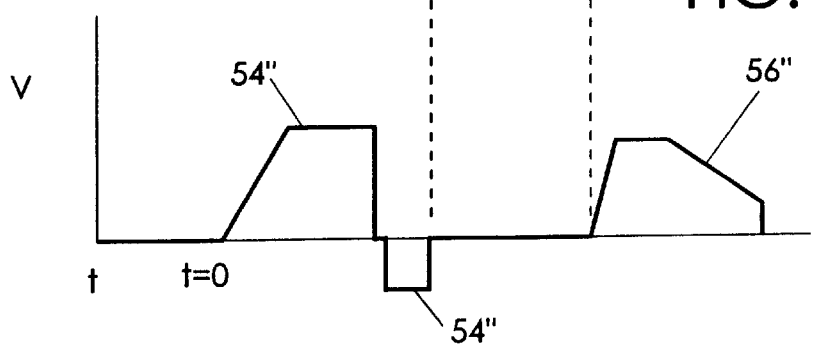
FIG. 7C is similar to FIG. 7A, and illustrates a shaped waveform.
Figure 7D:
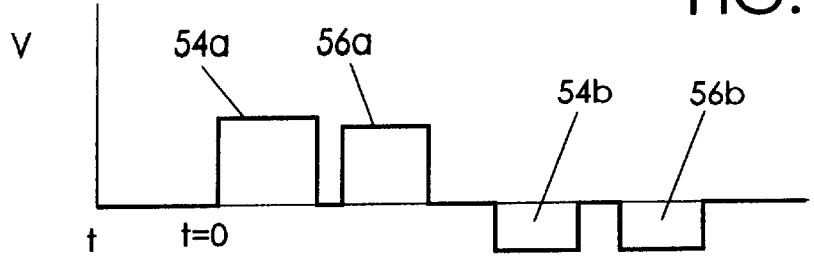
FIG. 7D is similar to FIG. 7A, and illustrates interleaved waveforms.

Alternatively, symmetrical waveforms having approximately equivalent first and second phase pulse segment duration times such as 3 ms/3 ms, monophasic waveforms or even reverse biphasic asymmetrical waveforms, or combinations of waveforms are also suitable. Further illustrated in FIGS. 7A and 7B, the second waveform 56, 56' are also asymmetric biphasic waveforms and along the same time duration as discussed for the first waveform 54. The waveforms may be stepped input waveforms 54', 56' as illustrated in FIG. 7B. The waveforms may be shaped, as illustrated by waveforms 54", 56" in FIG. 7C. Monophasic waveforms can be employed as either a first, second (see FIG. 7C) or even both pulse waveforms. The phases of biphasic waveforms may be separated in time by, for example, 0 to 200 ms. Additionally, the waveforms may be interleaved as illustrated in FIG. 7D, for example to sequentially provide a first pulse phase 54a to a first electrode pair such as a right atrium (RA) to distal coronary sinus (DCS) electrode pair, a second waveform 56a first phase to the second electrode pair such as a proximal coronary sinus (PCS) to left pulmonary artery LPA electrode pair, a first waveform second phase 54b to the first electrode pair, and then a second waveform second phase 56b to a second electrode pair. As will be appreciated by those skilled in the art, the shock sequence can be altered in any number of ways and still equivalently function in the manner intended herein.

In overview, an implantable atrial defibrillator for use in a system for the defibrillation of the atria of a patients heart by a first and second pair of atrial defibrillation electrodes comprises an implantable housing; an atrial fibrillation detector contained within the housing; and a pulse generator contained within the housing and operatively associated with the atrial fibrillation detector. The housing may be fabricated of any suitable biocompatible materials known to those skilled in the art. A power supply such as a battery operably associated with the pulse generator is typically contained within the housing. The pulse generator is configured for delivering a first atrial defibrillation pulse across the first pair of atrial defibrillation electrodes upon the detection of atrial fibrillation; and the pulse generator is configured for delivering a second atrial defibrillation pulse across the second pair of atrial defibrillation electrodes after the first defibrillation pulse. In one preferred embodiment, a subcutaneous electrode is located on the external surface of the housing of the implantable atrial defibrillator, as described in G. Bardy, U.S. Pat. No. 5,292,338 (the disclosure of which is incorporated by reference herein in its entirety). The defibrillator is then implanted in the left thoracic region of the patient (e.g., subcutaneously, in the left pectoral region) in accordance with known techniques, again as described in G. Bardy, U.S. Pat. No. 5,292,338. The implantable defibrillator may be used in combination with known leads or leads as described herein to provide a system as described herein.

One lead for insertion into the heart of a patient for use in combination with an atrial defibrillator of the present invention comprises an elongate catheter flexibly configured for insertion down the superior vena cava of the heart, into the right atrium, through the opening of the coronary sinus, through the proximal coronary sinus and into the distal coronary sinus or great cardiac vein of the heart to achieve an operable configuration therein; a first atrial defibrillation electrode connected to the catheter; and a second atrial defibrillation electrode connected to the catheter. The first and second atrial defibrillation electrodes are spaced apart on the catheter so that, when the catheter is in the operable configuration, the first atrial defibrillation electrode is positioned in the distal coronary sinus or great cardiac vein of the heart, and the second atrial defibrillation electrode is positioned in the proximal coronary sinus of the heart.

Another lead for insertion into the heart of a patient for use in combination with an atrial defibrillator of the present invention comprises an elongate catheter flexibly configured for insertion down the superior vena cava of the heart, into the right atrium, through the right ventricle, and into the pulmonary artery to achieve an operable configuration therein; a first atrial defibrillation electrode connected to the catheter; and a second atrial defibrillation electrode connected to the catheter. The first and second atrial defibrillation electrodes spaced apart on the catheter so that, when the catheter is in the operable configuration, the first atrial defibrillation electrode is positioned in the right atrium of the heart and the second atrial defibrillation electrode is positioned in the pulmonary artery. The lead may also include a third electrode connected to the catheter, with the third electrode spaced apart from the first and second atrial defibrillation electrodes so that, when the catheter is in the operable configuration, the third electrode is positioned in the left ventricle of the heart. The third electrode may be a monitoring electrode.

Systems as described above may be implanted in a patient by conventional surgical techniques, or techniques readily apparent to skilled surgeons in light of the disclosure provided herein, to provide an implanted atrial defibrillation system.

Additional features can also be added to the invention without affecting the function of the invention and result thereof. Such additional features include, but not limited to, safety features such as noise suppression or multiple wave monitoring devices (R and T), verification checking to reduce false positive, precardioversion warning, programmed delayed intervention, bipolar configured sensing electrodes, reducing the amount of charging voltage needed to charge a storage capacitor by "slow charging" and associated circuitry, intermittently activated defibrillation detector to reduce energy drain, a switching unit to minimize lines from the pulse generator, etc.

Although the atrial defibrillator has been described above as an implantable defibrillator, it will be appreciated by those of ordinary skill in the art that the invention could also be incorporated into an external atrial defibrillator which employs catheters to position the electrodes for a short time within a patient's heart. The external defibrillator could be of use for one-time cardioversion of atrial fibrillation or for patients who develop atrial fibrillation post-surgery.

The present invention is explained further in the following non-limiting example.

EXAMPLE 1

In this Example, as graphically illustrated in FIG. 8 (result H), a dual current pathway with first electrode pair RA-DCS and second electrode pair $CS_{OS}$ (PCS, supra)-LPA realized a significant decrease in delivered energy in a sheep model of atrial fibrillation (AF).

In five adult sheep (heart weight 342±21 gms), AF was induced with rapid atrial pacing. Transvenous defibrillation electrodes were positioned in the right atrial appendage (RAap), distal coronary sinus (DCS), proximal coronary sinus (CSos), left pulmonary artery (LPA), and right ventricular apex (RV). Seven single and seven dual current pathways were compared. A single capacitor biphasic waveform with the first phase 3 ms in duration and the second phase 1 ms in duration was delivered through each current pathway. The trailing edge voltage of each preceding first phase was equal to the leading edge voltage of the next phase. Atrial defibrillation thresholds (ADFT) were determined using a step up protocol, and probability of success curves were then determined by giving 10 shocks for each waveform starting at the ADFT using an up/down method with a 20 volt step size. The graph shows the electrode configurations and the mean and standard deviation of the total delivered energy for the 50% success points (E50). Dual current pathway "H" has a fourfold lower E50 than the standard single current pathway "A" (0.26±0.18 vs. 1.13±0.23 joules); also, pathway "H" had a significantly lower E50 than all other single and dual electrode configurations tested. Compared to the single current pathway ("A") being employed with the first implantable atrial defibrillators, atrial defibrillation thresholds can be markedly reduced by using dual current pathways.

The foregoing is illustrative of the present invention, and is not to be construed as limiting thereof. The invention is accordingly defined by the following claims, with equivalents of the claims to be included therein.

That which is claimed is:

1. An implantable system for the defibrillation of the atria of a human patient's heart, said system comprising:
   a first pair of atrial defibrillation electrodes configured for delivering a first atrial defibrillation pulse along a first current pathway in said heart;
   a pulse generator operatively associated with said first pair of atrial defibrillation electrodes for delivering said first atrial defibrillation pulse at not greater than 8 Joules;
   a second pair of atrial defibrillation electrodes configured for delivering a second atrial defibrillation pulse along a second current pathway in said heart, with said second current pathway different from said first current pathway; and
   a pulse generator operatively associated with said second pair of atrial defibrillation electrodes for delivering said second atrial defibrillation pulse at not greater than 8 Joules and after said first defibrillation pulse and without intervening monitoring of the efficacy of the first defibrillation pulse.

2. A system according to claim 1, wherein said first pair of atrial defibrillation electrodes comprises:
   a defibrillation electrode configured for positioning in the right atrium or superior vena cava of said heart; and
   a defibrillation electrode configured for positioning in the distal coronary sinus or great cardiac vein of said heart.

3. A system according to claim 1, wherein said second atrial defibrillation pulse follows said first atrial defibrillation pulse by 0 to 500 milliseconds.

4. A system according to claim 1, wherein said second pair of atrial defibrillation electrodes comprises:
   a defibrillation electrode configured for positioning in the proximal coronary sinus of said heart; and
   a defibrillation electrode configured for positioning anterior to the left atrium of said heart.

5. A system according to claim 1, wherein said second pair of atrial defibrillation electrodes comprises:
   a defibrillation electrode configured for positioning in the left pulmonary artery of said heart; and
   a defibrillation electrode configured for positioning in the right ventricle of said heart.

6. A system according to claim 1, wherein said second pair of atrial defibrillation electrodes comprises:
   a defibrillation electrode configured for positioning in the distal coronary sinus of said heart; and
   a defibrillation electrode configured for positioning in the right ventricle of said heart.

7. A system according to claim 1, wherein said second pair of atrial defibrillation electrodes comprises:
   a defibrillation electrode configured for positioning in the left pulmonary artery of said heart; and
   a defibrillation electrode configured for positioning in the right atrium of said heart.

8. A system according to claim 1, wherein said second pair of atrial defibrillation electrodes comprises:
   a defibrillation electrode configured for positioning in the left pulmonary artery of said heart; and
   a defibrillation electrode configured for positioning in the distal coronary sinus of said heart.

9. A system according to claim 1, wherein said second pair of atrial defibrillation electrodes comprises:
   a defibrillation electrode configured for positioning in the proximal coronary sinus of said heart; and
   a defibrillation electrode configured for positioning in the right atrium of said heart.

10. A system according to claim 1, wherein said second pair of atrial defibrillation electrodes comprises:
    a defibrillation electrode configured for positioning in the proximal coronary sinus of said heart; and
    a defibrillation electrode configured for positioning in the distal coronary sinus of said heart.

11. A system according to claim 1, further comprising:
    a monitoring electrode configured for monitoring the electrical activity of the ventricles of said heart, and
    a controller connected to said monitoring electrode configured for controlling the time of delivery of said first defibrillation pulse.

12. A system according to claim 11, wherein said monitoring electrode is configured for positioning in the right ventricle of said heart.

13. A system according to claim 1, said pulse generator including a switch, with said switch programmable to alter the coupling of said pulse generator to said atrial defibrillation electrodes.

14. A system according to claim 1, with said pulse generator including a capacitor and a switch operatively associated with said capacitor, said switch configured to deliver a biphasic pulse as said first atrial defibrillation pulse and a biphasic pulse as said second atrial defibrillation pulse.

15. An implantable system for the defibrillation of the atria of a human patient's heart, said system comprising:

a first defibrillation electrode configured for positioning in the right atrium or superior vena cava of said heart;

a second defibrillation electrode configured for positioning in the distal coronary sinus or great cardiac vein of said heart;

a pulse generator operatively associated with said first and second defibrillation electrodes for delivering a first defibrillation pulse not greater than 8 Joules between said first and second electrodes;

a third defibrillation electrode configured for positioning in the proximal coronary sinus of said heart;

a fourth defibrillation electrode configured for positioning anterior to the left atrium of said heart; and a pulse generator operatively associated with said third and fourth defibrillation electrodes for delivering a second defibrillation pulse not greater than 8 Joules between said third and fourth electrodes after said first defibrillation pulse and without intervening monitoring of the efficacy of the first defibrillation pulse.

16. A system according to claim 15, further comprising a first catheter, said first catheter having said second defibrillation electrode and said third defibrillation electrode connected thereto.

17. A system according to claim 16, further comprising a monitoring electrode configured for positioning in the right ventricle of said heart, and a controller connected to said monitoring electrode configured for controlling the time of delivery of said first defibrillation pulse.

18. A system according to claim 17, further comprising a second catheter and a third catheter, said second catheter having said first defibrillation electrode and said fourth defibrillation electrode connected thereto, said third catheter having said monitoring electrode connected thereto, and with said fourth defibrillation electrode configured for positioning in the pulmonary artery.

19. A system according to claim 17, further comprising a second catheter and a third catheter, said second catheter having said fourth defibrillation electrode connected thereto, said third catheter having said monitoring electrode and said first defibrillation electrode connected thereto, and with said fourth defibrillation electrode configured for positioning in the pulmonary artery.

20. A system according to claim 17, further comprising a second catheter and a third catheter, said second catheter having said first defibrillation electrode connected thereto, said third catheter having said monitoring electrode and said fourth defibrillation electrode connected thereto, and with said fourth defibrillation electrode configured for positioning in the pulmonary artery.

21. A system according to claim 17, further comprising a second catheter, said second catheter having said first defibrillation electrode said monitoring electrode, and said fourth defibrillation electrode connected thereto, and with said fourth defibrillation electrode configured for positioning in the pulmonary artery.

22. A system according to claim 17, further comprising a second catheter, a third catheter, and an implantable housing having said first pulse generator and said second pulse generator contained therein, said second catheter having said first defibrillation electrode connected thereto, said third catheter having said monitoring electrode connected thereto, and said housing having said fourth defibrillation electrode connected thereto, and with said housing configured for implantation anterior to the left atrium of the heart.

23. A system according to claim 15, further comprising an atrial fibrillation detector, and wherein said pulse generator is operatively associated with said atrial fibrillation detector and configured for delivering said first defibrillation pulse upon the detection of atrial fibrillation.

24. A lead for insertion into the heart of a patient for use in combination with an atrial defibrillator, said lead comprising:

an elongate catheter flexibly configured for insertion down the superior vena cava of the heart, into the right atrium, through the right ventricle, and into the pulmonary artery to achieve an operable configuration therein;

a first atrial defibrillation electrode connected to said catheter; and a second atrial defibrillation electrode connected to said catheter;

said first and second atrial defibrillation electrodes spaced apart on said catheter so that, when said catheter is in said operable configuration, said first atrial defibrillation electrode is positioned in the right atrium of the heart; and said second atrial defibrillation electrode is positioned in the pulmonary artery; and a third electrode connected to said catheter; said third electrode spaced apart from said first and second atrial defibrillation electrodes so that, when said catheter is in said operable configuration, said third electrode is positioned in the left ventricle of the heart.

25. A lead according to claim 24, wherein said third electrode is a monitoring electrode.

* * * * *

UNITED STATES PATENT AND TRADEMARK OFFICE
CERTIFICATE OF CORRECTION

PATENT NO.    : 6,006,131
DATED         : December 21, 1999
INVENTOR(S)   : Cooper et al.

It is certified that error appears in the above-identified patent and that said Letters Patent is hereby corrected as shown below:

Title page,
Please insert the following -- [*] Notice: This patent is subject to a terminal disclaimer. --

Column 13,
Line 25, should read as follows: -- 17. A system according to claim 5, further comprising a --

Signed and Sealed this

Fourth Day of March, 2003

JAMES E. ROGAN
*Director of the United States Patent and Trademark Office*